United States Patent [19]
Ravenscroft et al.

[11] Patent Number: 6,007,558
[45] Date of Patent: Dec. 28, 1999

[54] REMOVABLE EMBOLUS BLOOD CLOT FILTER

[75] Inventors: Adrian C. Ravenscroft, Milton; Stephen J. Kleshinski, Scituate, both of Mass.

[73] Assignee: Nitinol Medical Technologies, Inc., Boston, Mass.

[21] Appl. No.: 09/160,384

[22] Filed: Sep. 25, 1998

[51] Int. Cl.$^6$ .................................................. A61M 29/00
[52] U.S. Cl. ........................ 606/200; 606/194; 606/198
[58] Field of Search .................................. 606/200, 191, 606/194, 127, 198; 623/1

[56] References Cited

U.S. PATENT DOCUMENTS

| | | | |
|---|---|---|---|
| 4,425,908 | 1/1984 | Simon . | |
| 5,108,418 | 4/1992 | Lefebvre | 606/200 |
| 5,133,733 | 7/1992 | Rasmussen et al. | 606/200 |
| 5,242,462 | 9/1993 | El-Nounou et al. | 606/200 |
| 5,370,657 | 12/1994 | Irie . | |
| 5,601,595 | 2/1997 | Smith | 606/200 |
| 5,669,933 | 9/1997 | Simon et al. . | |
| 5,776,162 | 7/1998 | Kleshinski . | |
| 5,800,457 | 9/1998 | Gelbfish | 606/200 |
| 5,836,968 | 11/1998 | Simon et al. | 606/200 |

OTHER PUBLICATIONS

Cook "Bird's Nest" Vena Cava Filter, Cook Incorporated, a Cook Group Company, Nov. 1982.
"Metals that Remember", James Hansen, Science 81, pp. 44–47.
"A Vena Cava Filter Using Thermal Shape Memory Alloy", Morris Simon et al., Radiology, vol. 125, No. 1, Oct. 1977, pp. 89–94.
"Transvenous Devices for the Management of Pulmonary Embolism", Morris Simon et al., CardioVascular and Interventional Radiology, 3:308–313, 1980, pp. 112–120.

*Primary Examiner*—Michael Buiz
*Assistant Examiner*—Tina T. D. Pham
*Attorney, Agent, or Firm*—Sixbey, Friedman, Leedom & Ferguson; Daniel W. Sixbey

[57] ABSTRACT

A blood clot filter which is collapsible toward a central longitudinal axis into a collapsed configuration for insertion into a blood vessel and which is radially expandable outwardly from the longitudinal axis to an expanded configuration for contact with the inner wall of the blood vessel at two longitudinal spaced locations. A first plurality of spaced, elongate arms, in the expanded configuration of the filter, curve outwardly away from the longitudinal axis toward the leading end of the filter to form a first filter basket and to center a hub at the trailing end of the filter within the vessel. A second plurality of spaced elongate legs angle outwardly away from the longitudinal axis toward the leading edge of the filter in the expanded configuration thereof to form a second filter basket opening toward the leading end. To prevent longitudinal movement of the filter, the ends of these legs include hooks, at least a portion of which is of a reduced cross sectional area relative to the cross sectional area of the adjacent leg to permit the hooks to bend and straighten in response to withdrawal force.

19 Claims, 3 Drawing Sheets

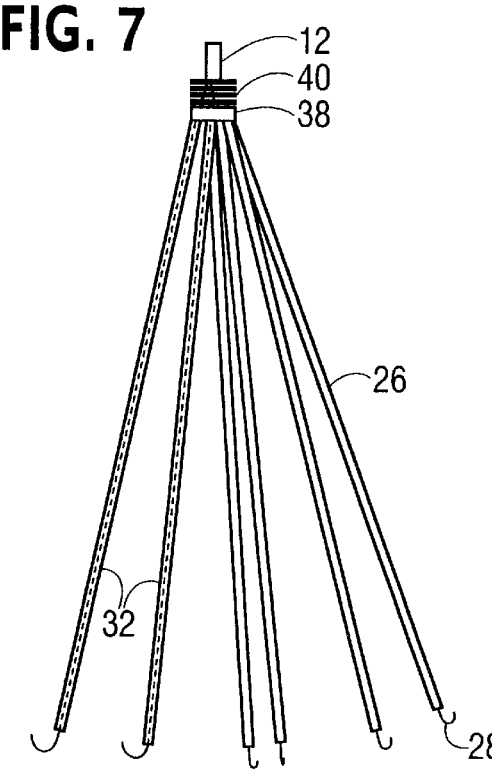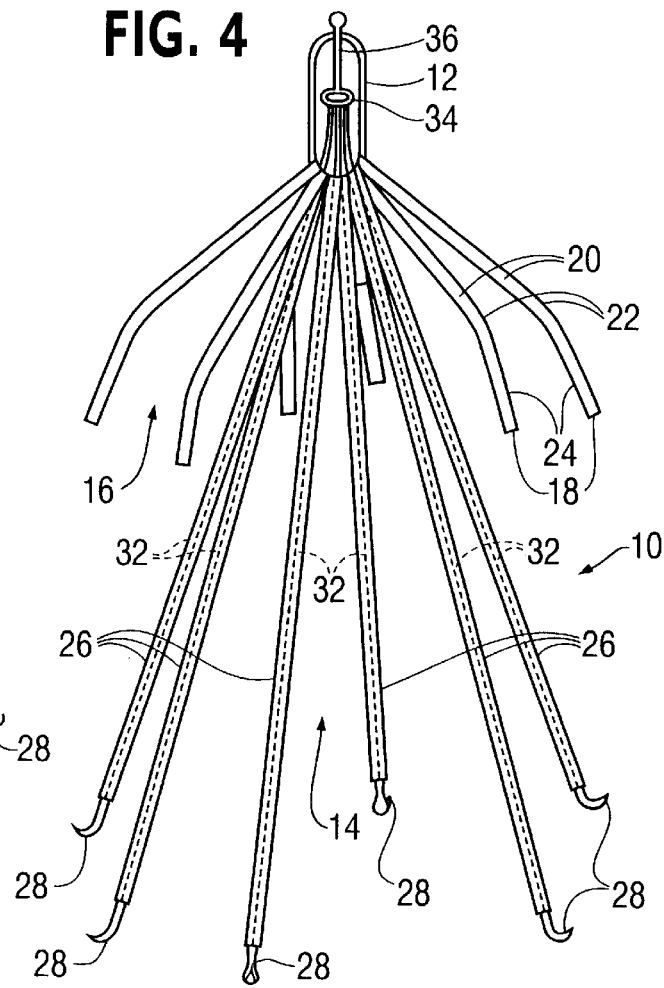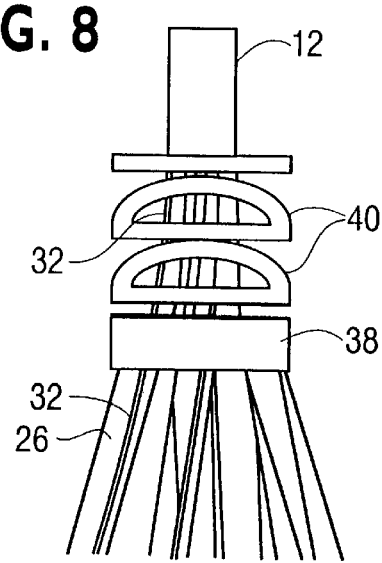

REMOVABLE EMBOLUS BLOOD CLOT FILTER

BACKGROUND OF THE INVENTION

In recent years, a number of medical devices have been designed which are adapted for compression into a small size to facilitate introduction into a vascular passageway and which are subsequently expandable into contact with the walls of the passageway. These devices, among others, include blood clot filters which expand and are held in position by engagement with the inner wall of a vein. It has been found to be advantageous to form such devices of a shape memory material having a first, relatively pliable low temperature condition and a second, relatively rigid high-temperature condition. By forming such devices of temperature responsive material, the device in a flexible and reduced stress state may be compressed and fit within the bore of a delivery catheter when exposed to a temperature below a predetermined transition temperature, but at temperatures at or above the transition temperature, the device expands and becomes relatively rigid.

Known self expanding medical devices have been formed of Nitinol, an alloy of titanium and nickel which provides the device with a thermal memory. The unique characteristic of this alloy is its thermally triggered shape memory, which allows a device constructed of the alloy to be cooled below a temperature transformation level to a martensitic state and thereby softened for loading into a catheter in a relatively compressed and elongated state, and to regain the memorized shape in an austenitic state when warmed to a selected temperature, above the temperature transformation level, such as human body temperature. The two interchangeable shapes are possible because of the two distinct microcrystalline structures that are interchangeable with a small variation in temperature. The temperature at which the device assumes its first configuration may be varied within wide limits by changing the composition of the alloy. Thus, while for human use the alloy may be focused on a transition temperature range close to 98.6° F., the alloy readily may be modified for use in animals with different body temperatures.

U.S. Pat. No. 4,425,908 to Simon discloses a very effective blood clot filter formed of thermal shape memory material. This filter, like most previously developed vena cava filters, is a permanent filter which, when once implanted, is designed to remain in place. Such filters include structure to anchor the filter in place within the vena cava, such as elongate diverging legs with hooked ends that penetrate the vessel wall and positively prevent migration in either direction longitudinally of the vessel. The hooks on filters of this type are rigid and will not bend, and within two to six weeks after a filter of this type has been implanted, the endothelium layer grows over the diverging legs and positively locks the hooks in place. Now any attempt to remove the filter results in a risk of injury to or rupture of the vena cava.

A number of medical procedures subject the patient to a short term risk of pulmonary embolism which can be alleviated by a filter implant. In such cases, patients are often adverse to receiving a permanent implant, for the risk of pulmonary embolism may disappear after a period of several weeks or months. However, most existing filters are not easily or safely removable after they have remained in place for more than two weeks, and consequently longer term temporary filters which do not result in the likelihood of injury to the vessel wall upon removal are not available.

In an attempt to provide a removable filter, two filter baskets have been formed along a central shaft which are conical in configuration, with each basket being formed by spaced struts radiating outwardly from a central hub for the basket. The central hubs are held apart by a compression unit, and the arms of the two baskets overlap so that the baskets face one another. Devices of this type require the use of two removal devices inserted at each end of the filter to draw the baskets apart and fracture the compression unit. The end sections of the arms are formed to lie in substantially parallel relationship to the vessel wall and the tips are inclined inwardly to preclude vessel wall penetration. If a device of this type is withdrawn before the endothelium layer grows over the arms, vessel wall damage is minimized. However, after growth of the endothelium layer the combined inward and longitudinal movement of the filter sections as they are drawn apart can tear this layer. U.S. Pat. No. 5,370,657 to Irie is illustrative of a prior art removable filter of this type which requries two removal devices.

SUMMARY OF THE INVENTION

It is a primary object of the present invention to provide a vessel implantable filter of shape memory material having temperature induced austenitic and martensite states which may be easily removed by a single removable device after an extended period of time without injuring the vessel wall.

Another object of the present invention is to provide a blood clot filter of Nitinol which operates in a temperature induced austenitic state to exert a force on the wall of a vessel by means of oppositely disposed legs to maintain the filter in place, but which may easily be removed after the endothelium layer has covered the ends of the filter legs without damage to the vessel wall.

A further object of the present invention is to provide a novel and improved filter having a group of arms and a group of legs which incline in the same direction from a central axis. The ends of the arms in the group of arms are oriented to engage a vessel wall to orient and center the filter in the vessel, and the ends of the legs of the group of legs are oriented to engage the vessel wall to prevent longitudinal movement of the filter along the vessel. The ends of the legs are provided with hooks configured to be more elastic than the legs to permit withdrawal from the endothelium layer without risk of injury to the vessel wall.

According to the invention, a resilient, longitudinally extanded blood clot filter is inwardly radially collapsible toward its longitudinal axis into a collapsed configuration for insertion into a vein, but is adapted for automatic radial expansion into contact with the inner wall of the vein at two longitudinally spaced peripheral locations therein. The filter has leading and trailing ends and comprises a plurality of wires. The wires, in the normal expanded configuration of the filter, are in the form of a plurality of elongated arms and legs with openings between the wires providing filter baskets opening at the leading end of the filter. The wires have peripheral portions for contact with the inner wall of the vein at two longitudinally spaced peripheral locations. The arms operate to center the filter while the legs terminate in hooks which anchor the filter but which straighten in response to force to facilitate removal of the filter.

To provide a filter that is inwardly radially collapsible from its normally expanded configuration toward its longitudinal axis into a collapsed configuration for insertion into a vein, the blood clot filter is preferably formed from a plurality of wire portions composed of a thermal shape memory material having a first, low-temperature condition and a second, high-temperature condition. The material in its low-temperature condition is relatively pliable (so that the wire portions may be straightened) and in its high-temperature condition is resiliently deformable and relatively rigid, and takes a pre-determined functional form.

In the high-temperature condition of the material, the filter comprises coaxial first and second filter baskets, each filter basket being generally symmetrical about the longitudinal axis of the filter with both filter baskets being concave relative to the filter leading end.

BRIEF DESCRIPTION OF THE DRAWINGS

FIG. 4 is a side view of a second embodiment of the blood clot filter of the present invention;

FIG. 7 is a view in side elevation of a hook withdrawal unit for a blood clot filter of the FIG. 4;

FIG. 8 is a view in side elevation of the hook withdrawal unit of FIG. 7 in a withdrawal configuration;

DETAILED DESCRIPTION

By forming the body of a blood clot filter of a Nitinol alloy material, such as Nitinol wire, transition between the martensitic and austenitic states of the material can be achieved by temperature transitions above and below a transition temperature or transition temperature range which is at or below body temperature. Such controlled temperature transitions have conventionally been employed to soften and contract the Nitinol filter body to facilitate insertion into a catheter and to subsequently expand and rigidify the body within a vascular or other passageway. Although the filters of the present invention are preferably formed from a temperature responsive shape memory material, such as Nitinol, they can also be formed of a compressible spring metal such as stainless steel or a suitable plastic.

Figure 1:
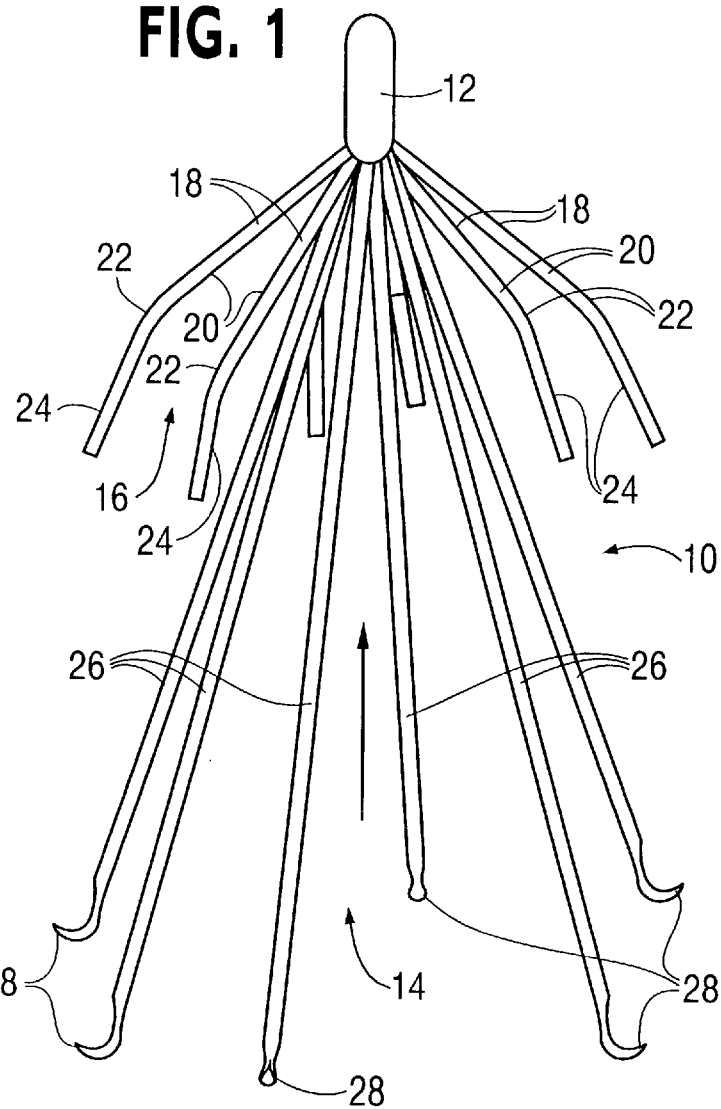
FIG. 1 is a view in side elevation of an expanded blood clot filter of the present invention.

Referring now to FIG. 1, an expanded blood clot filter 10 is illustrated which is made from sets of elongate metal wires. The wires are held together at one end at a hub 12 where they are plasma welded together and to the hub or otherwise joined. In the low temperature martensite phase of wires made of thermal shape memory material, the sets of wires can be straightened and held in a straight form that can pass through a length of fine plastic tubing with an internal diameter of approximately 2 mm (#8 French catheter). In its high temperature austenitic form, the filter 10 recovers a preformed filtering shape as illustrated by FIG. 1. Similarly, wires of spring metal can be straightened and compressed within a catheter or tube and will diverge into the filter shape of FIG. 1 when the tube is removed.

In its normal expanded configuration or preformed filtering shape, filter 10 is a double filter, having a first forwardly disposed filter basket section 14 at the forward end of the filter and a second forwardly disposed filter basket section 16. The two filter basket sections provide peripheral portions which can both engage the inner wall of the vein 17 at two longitudinally spaced locations and, the two filter basket sections are generally symmetrical about a longitudinal axis passing through the hub 12. On the other hand, the second forwardly disposed filter basket section 16, which is primarily a centering unit, may not touch the vessel wall on all sides.

The second filter basket section 16 is formed from short lengths of wire which form arms 18 that extend angularly, outwardly and then downwardly from the hub 12 toward the forward end of the filter 10. Each arm 18 has a first arm section 20 which extends angularly outwardly from the hub 12 to a shoulder 22, and an outer arm section 24 extends angularly from the shoulder toward the forward end of the filter. The outer arm sections 24 are substantially straight lengths with ends which lie on a circle at their maximum divergence and engage the wall of a vessel at a slight angle (preferably within a range of from ten to forty-five degrees) to center the hub 12 within the vessel. For a filter which is to be removed by grasping the hub 12, it is important for the hub to be centered. Normally, there are six wires 18 of equal length extending radially outward from the hub 12 and circumferentially spaced, such as for example bit sixty degrees of arc.

Figure 9:
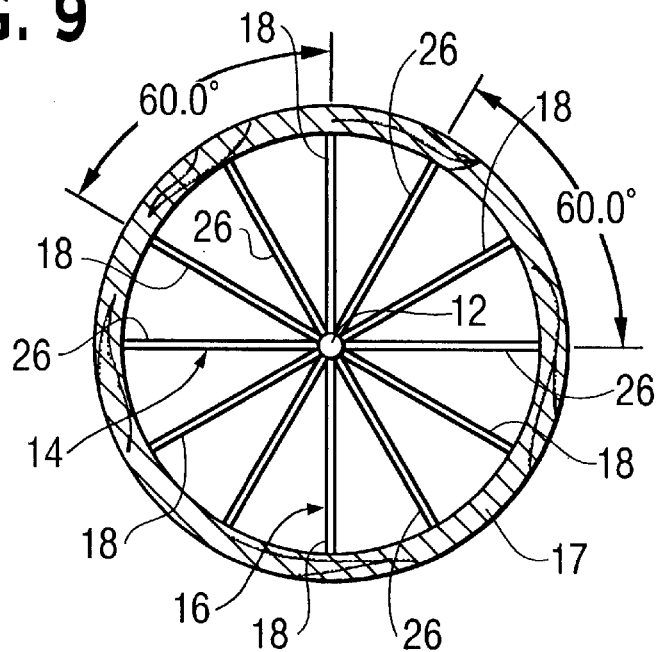
FIG. 9 is a cross sectional view of the blood clot filter of the present invention in place in a blood vessel.

The first filter basket section 14 is the primary filter and normally includes six circumferentially spaced straight wires 26 forming downwardly extending legs which tilt outwardly of the longitudinal axis of the filter 10 from the hub 12. The wires 26 may be of equal length, but normally they are not so that hooks 28 at the ends of the wires will fit within a catheter without becoming interconnected. The wires 26 are preferably much longer than the wires 18, and have tip sections which are uniquely formed, outwardly oriented hooks 28 which lie on a circle at the maximum divergence of the wires 26. The wires 26, in their expanded configuration of FIG. 1, are at a slight angle to the vessel wall 17, preferably within a range of from ten to forty-five degrees, while the hooks 28 penetrate the vessel wall to anchor the filter against movement. The wires 26 are radially offset relative to the wires 18 and may be positioned halfway between the wires 18 and also may be circumferentially spaced by sixty degrees of arc as shown in FIG. 9. Thus the combined filter basket sections 14 and 16 can provide a wire positioned at every thirty degrees of arc at the maximum divergence of the filter sections. With reference to the direction of blood flow in FIG. 1, the filter section 14 forms a concave filter basket opening toward the leading end of the filter 10 while the filter section 16 forms a concave filter basket opening toward the leading end of the filter 10 downstream of the filter section 14.

The structure of the hooks 28 is important. As in the case of hooks formed on the legs of previously known permanent vena cava filters, these hooks 28 penetrate the vessel wall when the filter 10 is expanded to anchor the filter in place and prevent filter migration longitudinally of the vessel in either direction. However, when these hooks are implanted and subsequently covered by the endothelium layer, they and the filter can be withdrawn without risk of injury or rupture to the vena cave.

Figure 2:
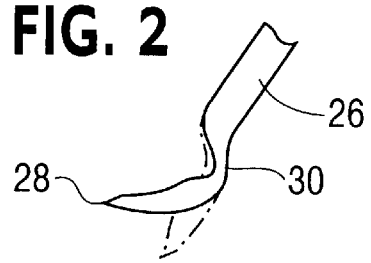
FIG. 2 is a view in side elevation of a hook for a leg of the filter of FIG. 1.

With reference to FIGS. 1 and 2, each hook 28 is provided with a juncture section 30 between the hook and the leg 26 to which the hook is attached. This juncture section is considerably reduced in cross section relative to the cross section of the leg 26 and the remainder of the hook. The juncture section is sized such that it is of sufficient stiffness when the legs 26 are expanded to permit the hook 28 to penetrate the vena cava wall. However, when the hook is to be withdrawn from the vessel wall, withdrawal force to which the hook is subjected will cause flexure in the juncture section 30 so that the hook moves toward a position parallel with the axis of the leg 26 as shown in broken lines in FIG. 2. With the hook so straightened, it can be withdrawn without tearing the vessel wall.

Figure 3:
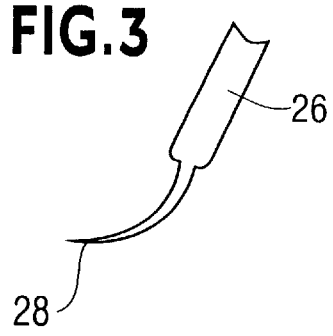
FIG. 3 is a in side elevation of a second embodiment of a hook for a leg of the filter of FIG. 1.

With reference to FIG. 3, it will be noted that the entire hook 28 can be formed with a cross section throughout its length which is less than that of the leg 26. This results in straightening of the hook over its entire length in response to a withdrawal force. This elasticity in the hook structure prevents the hook from tearing the vessel wall during withdrawal.

As previously indicated, while it is possible that the filler could be made from ductile metal alloys such as stainless steel, titanium, or elgiloy, it is preferable to make it from nitinol. Nitinol is a low modulus material which allows the arms and legs of the device to be designed to have low contact forces and pressures while still achieving sufficient anchoring strength to resist migration of the device. The load required to cause opening of the hooks 28 can be modulated to the forces required to resist migration. This is accomplished by changing the cross sectional area or geometry of the hooks, or by material selection.

In addition to temperature sensitivity, nitinol, when in the temperature induced austenitic state, is also subject to stress sensitivity which can cause the material to undergo a phase transformation from the austenitic to the martensitic state while the temperature of the material remains above the transition temperature level. By reducing a portion or all of the cross sectional area of the hooks 28 relative to that of the legs 26, stress is concentrated in the areas of reduced cross section when force is applied to remove the hooks from a vessel wall and the hooks become elastic and straighten. Thus the hooks, whether formed of nitinol, spring metal or plastic, are designed to bend toward a more straight configuration when a specific load is applied and spring back to their original shape once the load has been removed. The load or stress which is required to deform the hook can be correlated to the load applied to each hook of the device when it is fully occluded and the blood pressure in the vessel is allowed to reach 50 mm Hg. This load is approximately 70 gms on each leg on a six leg device for 50 mm Hg. pressure differential in a 28 mm vessel. The desired total load for the filter is desireably 420 gms, and more legs 26 with hooks 28 can be added to lower the load on each leg. The load on the filter would be correspondingly smaller in vessels of smaller diameter. The object is to have the hook perform as an anchoring mechanism at a pre-determined load which is consistent with a maximum pressure of 50 mm Hg. Having maintained its geometry at that load, the hook should begin to deform above the load and release at a load substantially less than that which would cause damage to the vessel tissue. It is the ability of the hook to straighten somewhat that allows for safe removal of the device from the vessel wall.

After the filter 10 has remained in place within a vessel for a period of time in excess of two weeks, the endothelium layer will grow over the hooks 28. However, since these hooks, when subjected to a withdrawal force become substantially straight sections of wire oriented at a small angle to the vessel wall, the filter can be removed leaving only six pin point lesions in the surface of the endothelium. To accomplish this, a catheter or similar tubular unit is inserted over the hub 12 and into engagement with the arms 18. While the hub 12 is held stationary, the catheter is moved downwardly forcing the arms 18 downwardly, and subsequently the arms 26 are engaged and forced downwardly thereby withdrawing the hooks 28 from the endothelium layer. Then the hub 12 is drawn into the catheter to collapse the entire filter 10 within the catheter. When the filter is formed from shape memory material, cooling fluid can be passed through the catheter to aid in collapsing the filter.

Figure 5:
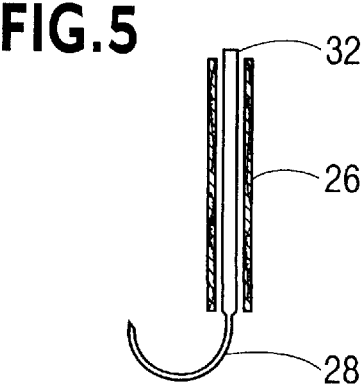
FIG. 5 is a sectional view of a portion of a leg for the filter of FIG. 4.
Figure 6:
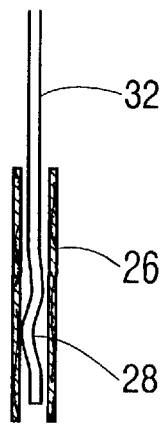
FIG. 6 is a sectional view of a portion of the leg for the filter of FIG. 4 with the hook withdrawn.

Referring now to FIGS. 4, 5 and 6, the legs of the filter 10 are formed as small tubes which open at one end into the hub 12. These legs may be formed of tubular plastic, spring metal, or thermal shape memory material. The hooks 28 are each formed at the ends of a long shaft 32, shown in broken lines in FIG. 4, which extends through a tubular leg 26 and into the hub 12 where it connects to a ring 34 on the end of a pull rod 36. The hook and the shaft therefor may be formed of wire or thermal shape memory material, and the cross sectional area of the hook is such that the hook will straighten and enter the tubular leg 26 as shown in FIG. 6 when the shaft 32 is pulled upward in FIG. 4 by the pull rod 36. Thus for filter removal, while the filter is still in place, the pull rod is grasped and the hooks are pulled into the tubular legs 26. Then a removal tube is moved over the arms 20 and 26 to collapse the filter.

A number of spring devices or similar structures may be provided adjacent to the hub 12 to draw the hooks 28 into the tubular legs 26 by means of the shafts 32. As shown by FIGS. 7 and 8, the hub 12 may be spaced from a sleeve 38 by a plurality of metal washers 40. The sleeve 38 receives and mounts the ends of the tubular legs 26 and, if arms are provided, the ends of the arms 20.

Thus, the sleeve 38 is fixed in place, and the shafts 32 extend through the open centers of the washers and are connected to the hub 12. The washers 40 are formed of thermal shape memory material, and below a temperature transformation level for the material, they lie flat against the sleeve 38 as shown in FIG. 7. However, when the washers are subjected to temperatures above their temperature transformation level, they bow upwardly along the longitudinal axis of the filter 10 as shown in FIG. 8 driving the hub 12 away from the sleeve 38 so that the hub draws the shafts 32 upwardly to pull the hooks 28 into the tubular legs 26.

When the legs 26 or the legs 26 and arms 20 are formed of thermal shape memory material, the temperature transformation level for this material will normally be body temperature or a temperature lower but close to body temperature. In this case, the temperature transformation level for the washers 40 will be higher than that for the arms 20 and legs 26 so that the washers will lie flat when the filter is in use. Heated saline solution or other known means can be applied to heat the washers 40 to temperatures above their temperature transformation level when the filter 10 is to be removed.

With this tubular leg design, the need to load the tissue of a supporting vessel to straighten and withdraw the hooks 28 is eliminated. Here, the load required to straighten a hook is created by the tubular leg 26.

Figure 10:
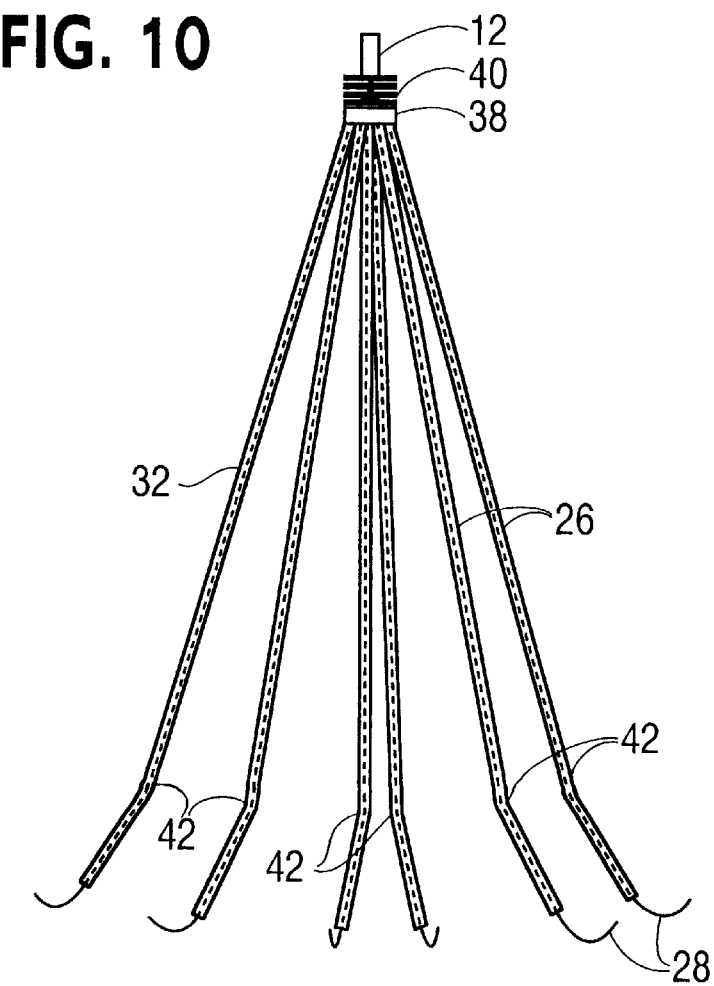
FIG. 10 is a view in side elevation of a third embodiment of a filter with a hook withdrawal unit.

Referring to FIG. 10, the tubular legs 26 may be angled outwardly from a shoulder 42 adjacent to but spaced from the outer end of each leg. When the legs are released from a compression in a catheter or other tube into a body vessel, this bend in each leg insures that the hooks 28 are, in effect, spring loaded in the tube and that they will not cross as they are deployed from the tube. Since the legs angle outwardly from the shoulders 42, the hooks 28 are rapidly deployed outwardly as the insertion tube is withdrawn toward the rear of the filter 10.

We claim:

1. A blood clot filter having a central longitudinal axis and which is collapsible into a collapsed configuration toward said longitudinal axis for insertion into a blood vessel and which is radially expandable outwardly from said longitudinal axis to an expanded configuration for contact with an inner wall of said blood vessel, said blood clot filter having leading and trailing ends and comprising:

a plurality of elongate, spaced legs which are tubular in configuration and have first and second ends, the first ends of said elongate spaced legs being mounted adjacent to said longitudinal axis and said plurality of elongate spaced legs being formed to extend outwardly away from said longitudinal axis to the second ends thereof which are spaced outwardly from the longitudinal axis in the expanded configuration of said filter, one or more of said plurality of elongate spaced legs having an outwardly curved hook terminating at a point at the second end thereof to engage and penetrate the vessel inner wall in the expanded configuration of said filter, said curved hook having an elongate shaft which is telescopically received in said elongate leg, the shaft being movable relative to said elongate leg to draw said hook into the elongate leg and straighten the hook, the entire cross sectional area along the length of the hook being of reduced size relative to the cross sectional area of the elongate leg, to permit said hook to bend toward a straightened configuration parallel to said elongate leg in response to force applied to remove said hook from the vessel inner wall, and an actuator mounted on said filter and connected to said shaft for moving the shaft relative to said elongate leg to draw said hook into the elongate leg.

2. The blood clot filter of claim 1 wherein said actuator means includes an actuator unit connected to each said shaft, said actuator unit being movable along said longitudinal axis away from the second ends of said elongate legs.

3. The blood clot filter of claim 2 wherein said actuator unit includes a drive unit formed of thermal shape memory material oriented to expand from a first collapsed configuration along said longitudinal axis to a second expanded configuration, said thermal shape memory material having a temperature transformation level below which said drive unit is in said first collapsed configuration and above which said drive unit expands along said longitudinal axis to said second expanded configuration.

4. The blood clot filter of claim 2 wherein said elongate spaced legs are formed of thermal shape memory material having a temperature transformation level below which said material is relatively pliable and compressible and above which said material is self-expandable to a substantially rigid, predetermined configuration, the temperature transformation level of the thermal shape memory material of said drive unit being higher than the temperature transformation level of the thermal shape memory material for said elongate legs.

5. A blood clot filter having a central longitudinal axis and which is collapsible into a collapsed configuration toward said longitudinal axis for insertion into a blood vessel and which is radially expandable outwardly from said longitudinal axis to an expanded configuration for contact with an inner wall of said blood vessel, said blood clot filter having leading and trailing ends and comprising:

a plurality of elongate, spaced legs having first and second ends with the first ends of said elongate spaced legs being mounted adjacent to said longitudinal axis and each of said legs being formed to extend outwardly away from said longitudinal axis to the second ends thereof which are spaced outwardly from said longitudinal axis in the expanded configuration of said filter, one or more of said plurality of elongate spaced legs is tubular in configuration and has an outwardly curved hook terminating at a point at the second end thereof to engage and penetrate the vessel inner wall in the expanded configuration of said filter, said curved hook having an elongate shaft which is telescopically received in said elongate leg, the entire cross sectional area along the length of the hook being of reduced size relative to the cross sectional area of the elongate leg to permit said hook to bend toward a straightened configuration parallel to said elongate leg in response to force applied to remove said hook from the vessel inner wall, and a plurality of spaced, elongate arms having first and second ends, said first ends of said arms being mounted adjacent to said longitudinal axis, said elongate spaced arms in the expanded configuration of said filter each extending angularly outward away from the longitudinal axis to an elbow spaced between the first and second ends of each said elongate arm and then angularly away from said elbow to the second end of said elongate arm, said elongate spaced legs extending toward the leading end of said filter to form a first filter basket and each said elongate arm angles outwardly from the longitudinal axis of said filter toward the leading end of said filter and then angles away from the elbow toward the leading end of said filter to form a second filter basket.

6. The blood clot filter of claim 5 wherein said shaft is movable relative to said elongate leg to draw said hook into said elongate leg and straighten said hook.

7. The blood clot filter of claim 6 wherein actuator means are mounted on said filter and connected to said shaft for moving said shaft relative to said elongate leg to draw said hook into said elongate leg.

8. The blood clot filter of claim 7 wherein actuator means includes an actuator unit connected to each said shaft, said actuator unit being movable along said longitudinal axis away from the second ends of said elongate spaced legs.

9. The blood clot filter of claim 8 wherein said actuator unit includes a drive unit formed of thermal shape memory material oriented to expand from a first collapsed configuration along said longitudinal axis to a second expanded configuration, said thermal shape memory material having a temperature transformation level below which said drive unit is in said first collapsed configuration and above which said drive unit expands along said longitudinal axis to said second expanded configuration.

10. The blood clot filter of claim 9 wherein said elongate spaced legs are formed of thermal shape memory material having a temperature transformation level below which said material is relatively pliable and compressible and above which said material is self-expandable to a substantially rigid, predetermined configuration, the temperature transformation level of the thermal shape memory material of said drive unit being higher than the temperature transformation level of the thermal shape memory material for said elongate spaced legs.

11. A blood clot filter having a central longitudinal axis and which is collapsible into a collapsed configuration toward said longitudinal axis for insertion into a blood vessel and which is radially expandable outwardly from said longitudinal axis to an expanded configuration for contact with an inner wall of said blood vessel, said blood clot filter having leading and trailing ends and comprising:

a plurality of elongate spaced legs having first and second ends, the first ends of said elongate spaced legs being mounted adjacent to said longitudinal axis and said plurality of elongate, spaced legs being formed to extend angularly outwardly away from said longitudinal axis toward the leading end of said filter to second ends of said elongate, spaced legs which are spaced outwardly from said longitudinal axis in the expanded configuration of said filter, and a plurality of spaced, elongate arms having first and second ends, said first ends of said spaced, elongate arms being mounted adjacent to said longitudinal axis, each of said spaced, elongate arms in the expanded configuration of said filter being formed to extend angularly outwardly away from the longitudinal axis of said filter toward the leading end of said filter to a shoulder spaced between said first and second ends of said elongate arm and then angularly inwardly from said shoulder in the direction of the longitudinal axis of said filter toward the filter leading end to the second end of the said elongate arm.

12. The blood clot filter of claim 11 wherein each of said spaced, elongate arms includes a first arm section which extends from the first end of said arm to said shoulder and a second arm section that extends from said shoulder to the second end of said arm, said first arm section angling outwardly in the expanded configuration of said filter from the first end thereof at a greater angle relative to the longitudinal axis of said filter than the outward angle of said elongate, spaced legs relative to said longitudinal axis of said filter.

13. The blood clot filter of claim 12 wherein the distance between the first and second ends of said elongate, spaced legs is greater than the distance between the first and second ends of said spaced, elongate arms.

14. The blood clot filter of claim 13 wherein said elongate spaced legs are each formed to be substantially straight between the first and second ends thereof and said spaced, elongate arms are each formed to have a substantially straight first arm section between said first end and the shoulder thereof and a substantially straight second arm section between the shoulder and the second end thereof.

15. The blood clot filter of claim 13 wherein said elongate legs extend toward the leading end of said filter to form a first filter basket and each said elongate arm angles outwardly from the longitudinal axis of said filter toward the leading end of said filter and then angles away from said elbow toward the leading end of said filter to form a second filter basket.

16. The blood clot filter of claim 14 wherein each of said elongate spaced legs and the second arm section of each of said spaced elongate arms is formed to engage the inner wall of said blood vessel at an angle within a range of from ten to forty five degrees adjacent to the respective second ends thereof in the expanded configuration of said filter.

17. The blood clot filter of claim 11 wherein one or more of said plurality of elongate spaced legs includes an outwardly curved hook terminating at a point at the second end thereof to engage and penetrate the vessel inner wall in the expanded configuration of said filter, said curved hook being formed with an elasticity sufficient to cause the hook to deform and straighten to permit withdrawal of the hook from the vessel inner wall in response to stress on the hook resulting from force applied to the trailing end of the filter to move the filter in a direction away from the filter leading end.

18. The blood clot filter of claim 17 wherein at least a portion of said hook spaced from said point is formed with a cross sectional area of reduced size relative to the cross sectional area of said elongate leg to permit said hook to bend toward a straightened configuration in response to force applied to the trailing end of said filter.

19. The blood clot filter of claim 17 wherein the elongate spaced legs and each outwardly curved hook included thereon are integrally formed of thermal shape memory material having a temperature transformation level below which the material is in a martensitic state and relatively pliable and compressible and above which the material is normally in an austenitic state and self-expandable to a substantially rigid, predetermined configuration, said material exhibiting stress sensitivity which can cause the material to transform to the martensitic state in response to stress while the temperature of the material remains above the temperature transformation level, each said outwardly curved hook being formed to be transformed from the austenitic state to the martensitic state in response to stress on the hook resulting from force applied to the trailing edge of the filter to move the filter away from the filter leading end while the elongate spaced legs remain in the austenitic state.

* * * * *